United States Patent [19]

VandenBerg

[11] Patent Number: Plant 6,113

[45] Date of Patent: Feb. 23, 1988

[54] CHRYSANTHEMUM PLANT NAMED BRONZE AROLA

[75] Inventor: Cornelis P. VandenBerg, Salinas, Calif.

[73] Assignee: Yoder Brothers, Inc., Barberton, Ohio

[21] Appl. No.: 832,779

[22] Filed: Feb. 25, 1986

[51] Int. Cl.[4] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Bronze Arola particularly characterized by its flat capitulum form; decorative capitulum type; greyed-orange ray floret color; diameter across face of capitulum of up to 6.5 cm. at maturity; uniform nine week photoperiodic flowering response to short days; medium plant height when grown as a pinched spray pot mum, and spreading branching pattern.

3 Drawing Figures

The present invention comprises a new and distinct cultivar of Chrysanthemum, botanically known as *Dentrenthema morifolium*, Ramat., previously *Chrysanthemum morifolium*, Ramat., and referred to by the cultivar name Bronze Arola.

Bronze Arola, identified as 79L19E04, is a product of a mutation program which had the objective of creating new Chrysanthemum cultivars that would expand the color range of an existing seedling while retaining all other original traits.

Bronze Arola was discovered and selected by Cornelis P. VandenBerg on Jan. 7, 1983 in a controlled environment in Salinas, Calif. as one flowering plant within a flowering block established as rooted cuttings from stock plants which had been exposed as unrooted cuttings to an X-ray source of 2200 rads. The irradiated parent cultivar was an unnamed seedling, identified as 79L19004.

The female parent of 79L19004 was the cultivar Tempo, disclosed in U.S. Plant Pat. No. 4,505. The male parent of 79L19004, identified as 7811008, was an unnamed seedling.

The first act of asexual reproduction of Bronze Arola was accomplished when vegetative cuttings were taken from the initial selection in April of 1983 in a controlled environment in Salinas, Calif. by technicians working under formulations established and supervised by Cornelis P. VandenBerg.

Horticultural examination of controlled flowerings of successive plantings has shown that the unique combination of characteristics as herein disclosed for Bronze Arola are firmly fixed and are retained through successive generations of asexual reproduction.

Bronze Arola has not been observed under all possible environmental conditions. The phenotype may vary significantly with variations in environment such as temperature, light intensity and day length.

The following observations, measurements and comparisons describe plants grown in Salinas, Calif. and Leamington, Canada under greenhouse conditions which approximate those generally used in commercial greenhouse practice.

The following traits have been repeatedly observed and are determined to be basic characteristics of Bronze Arola which, in combination, distinguish this Chrysanthemum as a new and distinct cultivar:

1. Flat capitulum form.
2. Decorative capitulum type.
3. Greyed-orange ray floret color.
4. Diameter across face of capitulum up to 6.5 cm. at maturity.
5. Uniform nine week photoperiodic flowering response to short days.
6. Medium plant height, requiring 10 to 14 long days prior to pinch, followed by 0 to 4 long days prior to short days, and one application of 2500 ppm B-9 SP after the beginning of short days to attain a flowered height of 25 to 35 cm. in 6" pots.
7. Spreading branching pattern.

The accompanying photographic drawings show typical inflorescence and leaf characteristics of Bronze Arola, with the colors being as nearly true as possible with illustrations of this type.

Sheet 1 is a color photograph of Bronze Arola grown as a pinched spray pot mum.

Sheet 2 is a black and white photograph of three views of the inflorescence of Bronze Arola.

Sheet 3 is a black and white photograph showing the upper and under sides of the leaves of Bronze Arola at three stages of development (mature, intermediate and immature).

Of the commercial cultivars known to the inventor, the most similar in comparison to Bronze Arola is the unpatented cultivar Torch grown as a spray pot mum. Reference is made to attached Chart A, which compares certain characteristics of Bronze Arola to the same characteristics of Torch. Similar traits are capitulum form and type and flowering response. Bronze Arola differs from Torch in ray floret color, branching pattern and plant height. Torch is recommended as both disbud pot mum and spray pot mum, while Bronze Arola is recommended as spray pot mum only.

In the following description, color references are made to The Royal Horticultural Society Colour Chart. The exact colors for corolla of ray florets are not represented in The Royal Horticultural Society Colour Chart, and the color values stated below are the closest color values to the actual color of Bronze Arola. The color values were determined on plant material grown in Salinas, Calif. on Aug. 16, 1985.

Classification:

*Botanical.*—*Dentrenthema morifolium,* Ramat., cv Bronze Arola.

*Commercial.*—Spray decorative pot mum.

INFLORESCENCE

A. Capitulum:

*Form.*—Flat.

*Type.*—Decorative.

*Diameter across face.*—Up to 6.5 cm. at maturity.

B. Corolla of ray florets:

*Color (general tonality from a distance of three meters).*—Greyed-orange.

*Color (upper surface).*—167D overlaid with 179A.

*Color (under surface).*—163D.

*Shape.*—Oblong.

C. Corolla of disc florets:

*Color (Mature).*—9A.

*Color (immature).*—2B.

D. Reproductive organs:

*Androecium.*—Present disc florets only; very few, scant pollen.

*Gynoecium.*—Present both ray and disc florets.

PLANT

A. General appearance:

*Height.*—Medium; 25 to 35 cm. as a flowering pot plant given 10 to 14 long days before pinch and 0 to 4 long days before start of short days, with one application of 2500 ppm B-9 SP.

*Branching pattern.*—Spreading and prolific.

B. Foliage:

*Color (upper surface).*—137A.

*Color (under surface).*—137B.

*Shape.*—Moderately lobed and slightly serrated.

CHART A

COMPARISON OF BRONZE AROLA AND TORCH

| CULTIVAR | RAY FLORET COLOR | CAPITULUM FORM AND TYPE | BRANCHING PATTERN |
|---|---|---|---|
| BRONZE AROLA | GREYED-ORANGE | FLAT DECORATIVE | SPREADING |
| TORCH | BRONZE | FLAT DECORATIVE | UPRIGHT |

| CULTIVAR | DIAMETER ACROSS FACE OF CAPITULUM | PLANT HEIGHT | FLOWERING RESPONSE PERIOD |
|---|---|---|---|
| BRONZE AROLA | UP TO 6.5 cm. | MEDIUM | NINE WEEKS |
| TORCH | UP TO 7.0 cm. | SHORT | NINE WEEKS |

COMPARISONS MADE OF PLANTS GROWN AS SPRAY POT MUMS IN SALINAS, CALIFORNIA

I claim:

1. A new and distinct Chrysanthemum plant named Bronze Arola, as described and illustrated, and particularly characterized as to uniqueness by the combined characteristics of flat capitulum form; decorative capitulum type; greyed-orange ray floret color; diameter across face of capitulum of up to 6.5 cm. at maturity; uniform nine week photoperiodic flowering response to short days; medium plant height when grown as a pinched spray pot mum, and spreading branching pattern.

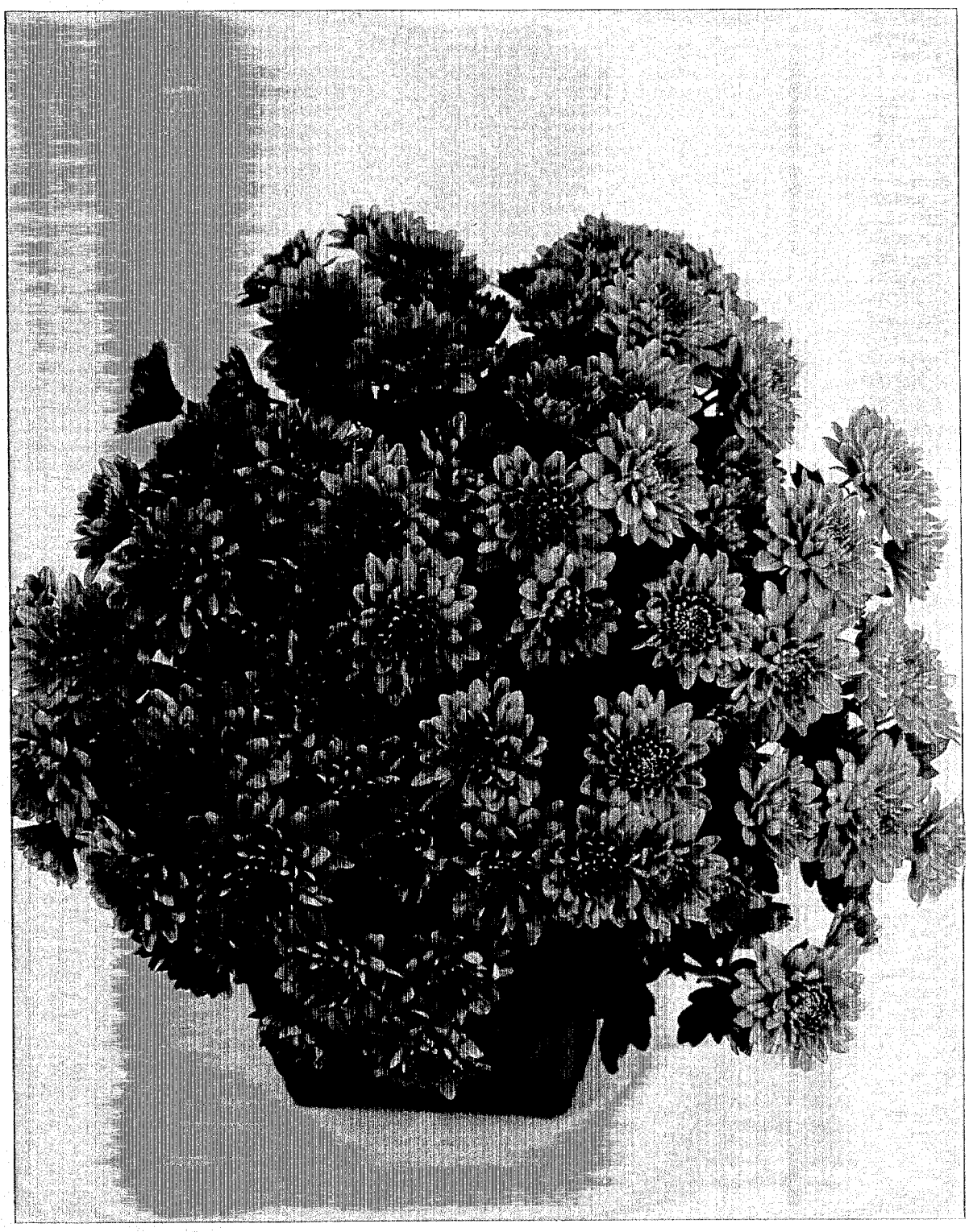

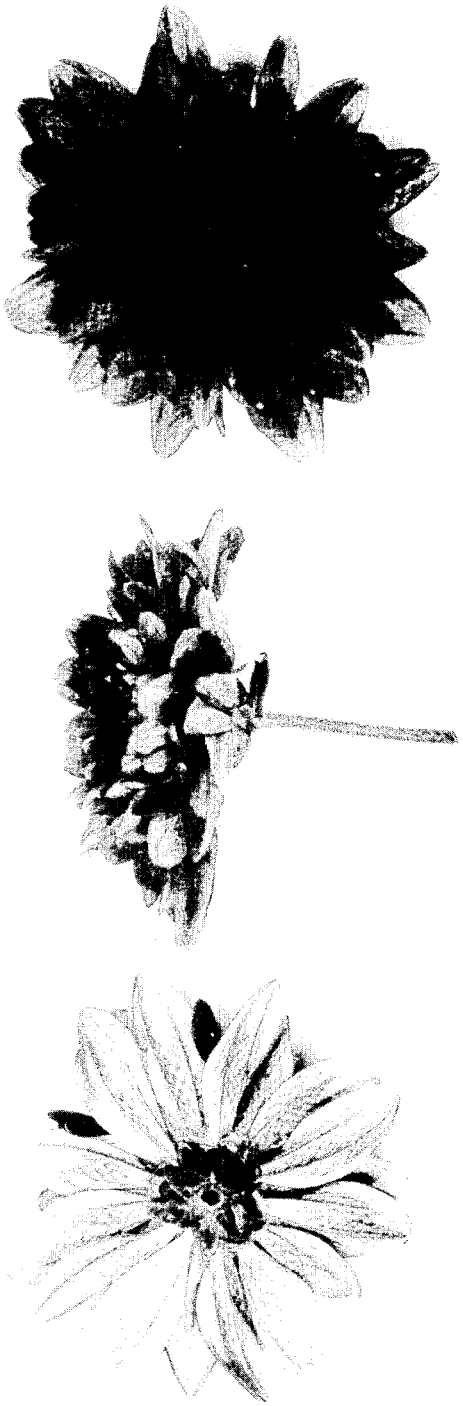

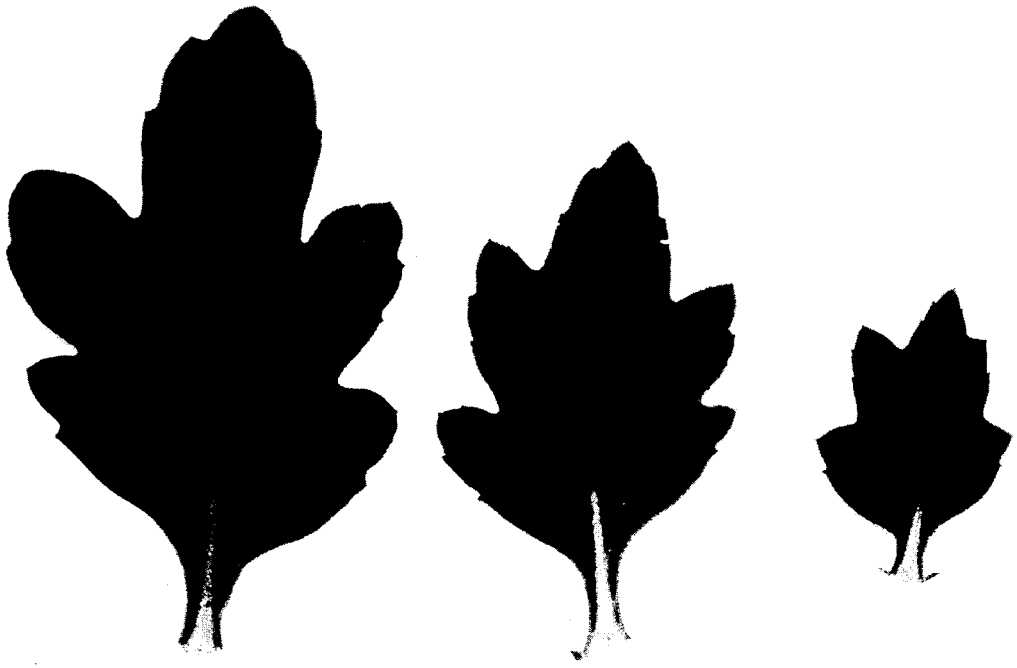
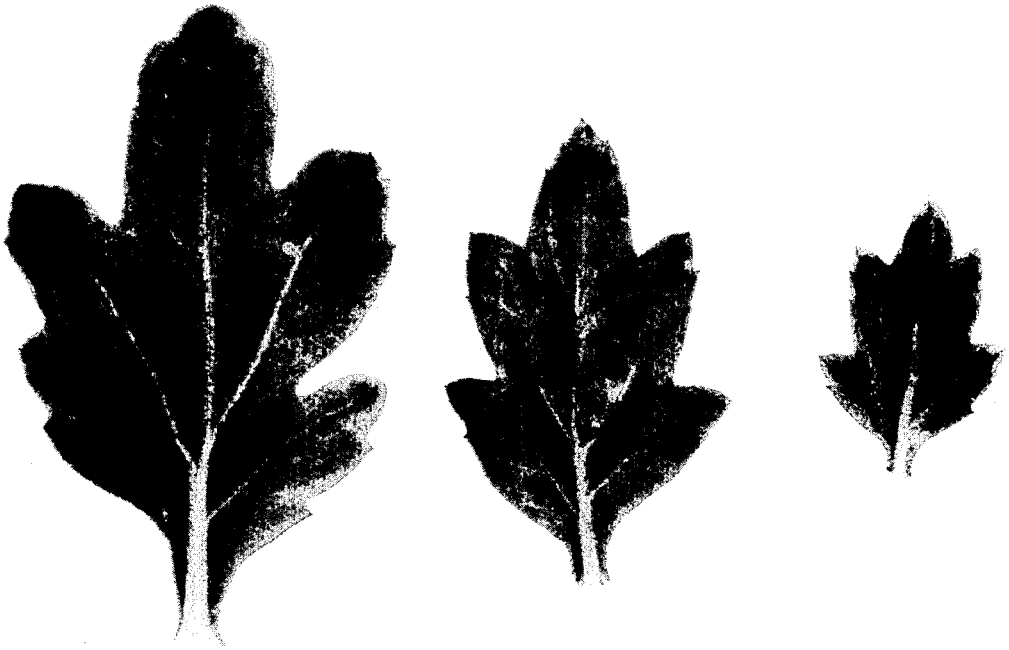

* * * * *